United States Patent [19]

Ranade et al.

[11] Patent Number: 5,141,810

[45] Date of Patent: Aug. 25, 1992

[54] MEANS FOR CONSTRAINING A RUMEN DRUG DELIVERY DEVICE IN A ROLLED CONFIGURATION

[75] Inventors: Gautam R. Ranade, East Lyme; Alan C. Curtiss, Old Lyme, both of Conn.

[73] Assignee: Pfizer Inc., New York, N.Y.

[21] Appl. No.: 253,018

[22] Filed: Oct. 4, 1988

[51] Int. Cl.$^5$ ................................................ C09J 7/02
[52] U.S. Cl. ................................. 428/350; 428/354; 428/355
[58] Field of Search ............... 428/350, 354, 355, 536, 428/509

[56] References Cited

U.S. PATENT DOCUMENTS

| | | | |
|---|---|---|---|
| 2,770,555 | 11/1956 | Cornwell | 428/536 |
| 3,441,430 | 4/1969 | Peterson | 117/68.5 |
| 3,865,770 | 2/1975 | Blake | 260/27 R |
| 4,228,149 | 10/1980 | Brewer et al. | 424/14 |
| 4,386,859 | 6/1983 | Andrione | 384/420 |
| 4,413,080 | 11/1983 | Blake | 524/187 |
| 4,431,010 | 2/1984 | Seraguoli | 131/94 |
| 4,431,162 | 2/1984 | Carlson | 251/144 |
| 4,569,960 | 2/1986 | Blake | 524/145 |
| 4,585,666 | 4/1986 | Lambert | 427/2 |
| 4,601,893 | 7/1986 | Cardinal | 424/15 |

FOREIGN PATENT DOCUMENTS 0021758  6/1980  European Pat. Off. .
2918746 11/1980  Fed. Rep. of Germany .

*Primary Examiner*—Jenna L. Davis
*Attorney, Agent, or Firm*—Peter C. Richardson; Paul H. Ginsburg; Grover F. Fuller, Jr.

[57] ABSTRACT

Improved means for constraining a rumen drug delivery device in a rolled configuration, said means comprising a laminate, which may be perforated, comprising a water-permeable material having a low friction surface in the presence of water, said material being bonded by means of a water-dispersible pressure sensitive adhesive to a repulpable tape, said tape having said water-dispersible pressure sensitive adhesive on both its surfaces; a laminate comprising a flexible, water-permeable polymeric material bonded between the low friction surface material and the repulpable tape; and devices constrained by said means.

6 Claims, No Drawings

5,141,810

MEANS FOR CONSTRAINING A RUMEN DRUG DELIVERY DEVICE IN A ROLLED CONFIGURATION

BACKGROUND OF THE INVENTION

1. Field of the Invention

This invention relates to improved means for constraining a rumen drug delivery devices in a rolled configuration. More particularly, it relates to laminates comprising a water permeable material having a low friction surface in the presence of water, said material being bonded to a repulpable tape having a water-dispersible adhesive on both surfaces; to laminates comprising a flexible, water-permeable polymeric material bonded between the low friction surface material and the repulpable tape; and to devices so constrained.

2. Description of Related Art

Rumen drug delivery devices constrained in a rolled-up configuration by appropriate constraining means are disclosed in U.S. Pat. Nos. 4,228,149 and 4,601,893, the disclosures of which are incorporated herein by reference. U.S. Pat. No. 4,228,149 discloses sheets of drug-containing ethylene vinyl acetate copolymer, which may be coated on both surfaces by a water soluble polymer film, constrained in a rolled-up configuration. U.S. Pat. No. 4,601,893 teaches laminate devices comprising a drug-containing ethylene vinyl acetate copolymer sheet sandwiched between two coextensive films of ethylene vinyl acetate copolymer and having one or more macro-perforations extending through all laminae, said laminae being constrained in a rolled-up configuration. U.S. application Ser. No. 170,495, filed Mar. 21, 1988, describes improved delivery devices of the type disclosed in U.S. Pat. No. 4,601,893. The improved devices are identical to those of U.S. Pat. No. 4,601,893 in construction but, in order to enhance their unrolling in the use environment, have been subjected to an annealing process prior to being constrained in a rolled configuration. The annealing process is conducted at a temperature of from about 40° C. to about 80° C., a range of about 43° to 60° C. being preferred. The time of annealing varies with the temperature of annealing. Further, the time and temperature vary with the manner in which the devices being annealed are arranged for the annealing step. The U.S. Pat. No. 4,601,893 type devices can be punched or cut to their approximate or actual size prior to annealing or the sheets from which the individual devices are punched can be annealed prior to punching out individual devices. The individual devices or sheets can be annealed individually or they can be stacked one upon the other to a height determined only by the size of the annealing equipment. The sheets can also be rolled for ease of handling prior to annealing and punching. In any case, stacking of the devices or sheets or rolling of the sheets generally requires temperatures toward the lower end of the indicated range and times toward the upper end of the range. Each arrangement requires determination of the conditions for optimum annealing. Temperatures which are too high may cause sticking of stacked devices, sheets or rolled sheets. Lower temperatures and longer times are best suited for stacked or rolled materials. For example, a roll of sheet material comprising a core 0.075 inches (1.91 mm) thick and outer layers each 0.05 inch (1.27 mm) thick, rolled on a 14 inch (35.56 cm) spindle to an overall diameter of 94 inches (238.76 cm), is desirably annealed for up to 96 hours at 43° C. Thus, considering the parameters of temperature and overall thickness of the material to be annealed from about 96 to 4 hours is practical.

A further modification of the delivery devices of U.S. Pat. No. 4,601,893 is described in U.S. application Ser. No. 170,529, filed Mar. 21, 1988. Said modification comprises U.S. Pat. No. 4,601,893 type devices which have been coated on one side with an elastomer prior to being constrained in a rolled configuration. The elastomer coated side becomes the outer side of the device when the device is placed in a rolled configuration. The elastomer coated side improves the elasticity of the devices such that they recover or unroll from their constrained configuration to a greater extent and at a faster rate. The term "elastomer" as used herein is intended to embrace materials that, when stretched, snap back to their original or near-original shape. More specifically, it embraces thermoset and thermoplastic elastomers or elastoplastics, representative of which are styrene-diene block copolymers, polyurethanes, nitrile rubbers, olefinics and copolyester ethers, and preferably silicon rubbers (e.g. polydimethylsiloxanes). In each of said patents and applications the constraining means comprises a biodegradable material such as gelatin string or tape, water soluble adhesive or paper.

Within the use environment; i.e., the rumen, the constraining means is dissolved, destroyed, ruptured or otherwise removed to allow the rolled-up device to revert to its original, or near-original sheet configuration to prevent its expulsion from the rumen.

It has been observed that the prior art devices described above are sometimes expelled by the ruminant because of untimely removal of the constraining means within the rumen. Additionally, difficulty is often encountered upon oral administration of the constrained devices to young ruminants. Premature removal of the constraining means and subsequent unrolling of the constrained device or slow transit of the constrained device can lead to dosing problems. Thus, the need for improved constraining means for rumen drug delivery devices which will facilitate dosing of ruminants therewith and enable timely change of configuration in the rumen and eliminate expulsion of the device by the ruminant.

SUMMARY OF THE INVENTION

There has now been found improved constraining means which overcome the above-cited difficulties. The herein-described constraining means provide a low friction surface to facilitate dosing of the device, afford timely change in geometry of the rolled-up device within the rumen, avoid premature unrolling of the devices on dosing, are stable and non-toxic.

DETAILED DESCRIPTION OF THE INVENTION

The improved constraining means of this invention comprises a water-permeable material having a low friction surface in the presence of water, said material being bonded by means of a water-dispersible pressure sensitive adhesive to a repulpable tape which is coated on both surfaces with said adhesive. A modification of the above-described laminate comprises one having a flexible, water-permeable polymeric material bonded between the low friction surface material and the repulpable tape. A still further modification comprises a laminate comprising a flexible, water-permeable polymeric material sandwiched between two sheets of a water-permeable material having a low friction surface in the presence of water, one surface of which is bonded by means of a water-dispersible pressure sensitive adhesive to a repulpable tape which is coated on both surfaces (doubly coated) with said adhesive. Also included in this invention are rolled-up rumen drug delivery devices constrained by the herein-described improved constraining means.

Water-dispersible pressure sensitive tapes and repulpable tapes coated with said water-dispersible pressure sensitive adhesives are described in U.S. Pat. Nos. 3,865,770; 3,441,430; 4,413,080; and 4,569,960. Such tapes find extensive use in the paper-making industry. The disclosures of each of said patents is incorporated herein by reference.

The favored water-permeable material having a low friction surface in the presence of water is nitrocellulose. As the outermost, or top layer, of the laminates described herein, the nitrocellulose facilitates oral administration of the constrained devices in view of the low-friction surface which it acquires in the presence of the saliva in the ruminant's esophageal passage.

In one form of the herein described constraining means, the nitrocellulose film is bonded directly to one surface of the doubly adhesive coated repulpable tape. The other adhesive coated surface, of the tape is, of course, bonded to the rolled-up drug delivery device so as to constrain it in said configuration. This form of constraining means may, if increased flow of environmental fluid to the water dispersible adhesive is desired, be perforated, especially with macroholes ranging from about 0.5-5 mm in diameter, prior to its being applied to the rolled-up device. The holes are normally circular but could be any shape such as, for example, ovals, triangles, squares, hexagons, etc. The perforations tend to accelerate removal of the constraining means.

In a modified, and favored, form of the improved constraining means of this invention, a flexible, water-permeable polymeric material, preferably cellophane, is bonded between the low friction surface material and the repulpable tape. The cellophane serves to enhance removal of the constraining means and unrolling of the rolled-up device. In addition to cellophane other water-permeable polymers, such as polyvinyl acetate, polymethylmethacrylate, polyethylmethacrylate, polyvinylchloride, cellulose acetate and polydimethylsiloxane, can be used.

A preferred modification of the improved constraining means of this invention comprises a laminate comprising a flexible, water-permeable polymeric material, such as is described above, sandwiched between two sheets of a water-permeable material (e.g. nitrocellulose) having a low friction surface in the presence of water, one surface of which is bonded to a repulpable tape doubly coated with a water-dispersible pressure sensitive adhesive. The thickness of said coated cellophane can range from about 0.3 to 3.0 mils (0.0076 to 0.076 mm.). Cellophane coated on both surfaces with nitrocellulose, i.e., sandwiched between nitrocellulose, is commercially available from BCL America, Inc. of Malvern, PA. 19355, product grade 345 PS-41. It has a thickness of about 0.9 mil (0.023 mm.).

Each of the forms of the constraining means described herein may optionally have macroperforations made in them, especially at that portion thereof where the said means abut or overlap when placed about the rolled-up delivery device to enhance unrolling of the device in the use environment.

The laminates of this invention are conveniently constructed by contacting the individual layers of the lamina, e.g., nitrocellulose, or cellophane coated on both sides with nitrocellulose, with the repulpable tape doubly coated with a water-dispersible pressure sensitive adhesive. Suitable water-dispersible pressure sensitive adhesives are well known in the art.

Representative water-dispersible pressure sensitive adhesives are those comprising a copolymer of monomeric acrylic acid esters and vinyl carboxylic acid monomer, said copolymer being partially neutralized with a secondary or tertiary alkanolamine, or an alkali metal hydroxide. Oily plasticizing compounds such as water-soluble polyoxyethylenes; and tackifiers such as reaction products of acid rosins and alkanolamines are added thereto. Such adhesives and their use to make repulpable tapes are described in U.S. Pat. Nos. 3,865,770; 4,413,080, 4,569,960 and references cited therein, incorporated herein by reference.

Illustrative of such adhesives described in said patents are those comprising:

(I)
(a) a copolymer of monomers consisting essentially of
(1) about 90-20 parts by weight monomeric acrylic acid ester of non-tertiary alkyl alcohol the molecules of which have 1 to 4 carbon atoms; and
(2) about 10-80 parts by weight vinyl carboxylic acid monomer copolymerizable with said acrylic acid ester, at least a number of the carboxyl groups in said acid monomers sufficient to constitute about 3-22% the weight of said copolymer, having been partially neutralized by reaction with a secondary or tertiary alkanolamine containing at least 4 carbon atoms; and
(b) 0-400 parts by weight of at least one water-dispersible tack-promoting material selected from the class consisting of the oily plasticizing water-soluble polyoxyethylene compounds and the tackifying reaction products of acid rosins and alkanolamines; or (II) the blended reaction product of
(a) 100 parts by weight of a copolymer of monomers consisting essentially of
(1) about 75-85 weight percent of at least one monomeric acrylic acid ester of nontertiary alkyl alcohol, and correspondingly,
(2) about 25-15 weight percent of vinyl carboxylic acid,
(b) about 35-100 parts by weight of acidic rosin or rosin derivative,
(c) sufficient potassium hydroxide to neutralize about 30-45% of the combined carboxyl groups of the copolymer and rosin or rosin derivative,
(d) sufficient sodium hydroxide, lithium hydroxide, or a combination of sodium and lithium hydroxide to neutralize about 20-45% of said carboxyl groups, and
(e) about 100-225 parts by weight of oily plasticizing water-soluble polyoxyethylene compound; or (III) the blended reaction product of
(a) 100 parts by weight of a copolymer of monomers consisting essentially of (1) about 60–85 weight percent of at least one monomeric acrylic acid ester of nontertiary alkyl alcohol having 4–14 carbon atoms, and correspondingly, (2) about 40–15 weight percent of vinyl carboxylic acid, (b) about 50 to 250 parts by weight of ethoxylated plasticizing components, sufficient to impart adhesion values such as to cause the adhesive to delaminate kraft paper when tested as described herein, consisting essentially of at least one of the following:

(1) up to about 125 parts by weight, but not so much as to cause adhesive separation, of one or more OH-functional ethoxylated plasticizers and (2) one or more electrolyte-tolerant complex and acidic esters of phosphoric acid and an ethoxylated nonionic surfactant, and (c) alkaline hydroxide consisting essentially of (1) sodium hydroxide, lithium hydroxide, or both sodium hydroxide and lithium hydroxide, in an amount sufficient to enhance shear strength and minimize bleeding but insufficient to cause separation of any OH-functional ethoxylated plasticizer present, not exceeding about 0.07 hydroxyl equivalent if OH-functional ethoxylated plasticizer is the only plasticizing component present, and (2) potassium hydroxide in an amount sufficient to promote water solubility.

The constraining means of this invention should not substantially increase the overall diameter of the constrained device at the point of constrainment to a thickness that would give rise to dosing problems when the constrained device is administered to a rumen. This relationship between the thickness (diameter) of the rolled-up device and that of the constraining means will be recognized by those skilled in the art. Said individuals will appreciate the need to maintain the thickness of the constraining means to a minimum thickness consistent with acceptable times of removal of the constraining means in the use environment. In general, constraining means of this invention having a thickness of from about 1.3 to 10.0 mils (0.0013 to 0.010 inch; or 0.033 to 0.254 ml.) afford acceptable release times. Such constraining means are especially valuable when used to constrain delivery devices of U.S. Pat. Nos. 4,601,893 and 4,228,149. A typical device of U.S. Pat. No. 4,601,893 for use in cattle, has, when rolled-up, a diameter of about 2.54 cm.

The point of greatest tension in the constraining means occurs at that segment of the roll where the constraining means bridges the gap formed by its contact with the terminal edge of the outer layer of the rolled-up device and the surface of the layer upon said outer layer ends. The effect of this tension can be minimized by doubling the thickness of the overall length of the constraining means used. Alternatively, the effect can be minimized by placing a reinforcing strip of said constraining means having the thickness disclosed above over said segment.

As will be appreciated the constraining means used can be of sufficient length as to completely wrap about the rolled-up device, the ends thereof forming a butt joint. Alternatively, the constraining means can be of such a length that the ends thereof overlap to a lesser or greater extent when said means is placed about a rolled-up device. The extent of overlap should, for economic reasons, be less than that which would result in a double thickness of constraining means. Still further, the constraining means need not entirely wrap about the rolled-up device. It should, at the least, be in contact with the terminal end of the outer layer of the rolled-up device and the surface of the layer upon which said outer layer ends. The favored length of constraining means is that required to completely wrap about the rolled-up device.

The improved constraining means of this invention are readily prepared by laminating the adhesive coated repulpable tape to the water-permeable polymeric material having a low friction surface in the presence of water, e.g., nitrocellulose; or to the nitrocellulose coated cellophane, by known methods, care being taken to avoid formation of bubbles or wrinkles. The laminated tape is then cut to desired size. Perforations may be conveniently made either before or after cutting of the laminated tape.

The removability of the constraining means of this invention in the use environment, e.g., the rumen of a ruminant, is determined by in vitro or in vivo methods. The in vitro method comprises placing the constrained device in water, or more appropriately a synthetic rumen fluid, at 40° C. on an incubator shaker (ca.80 excursions per minute) and observing the time required for unrolling of the constrained device. The in vivo method comprises administering the constrained device to a fistulated ruminant and observing the time required for unrolling of the constrained device.

To further minimize dosing problems, the constrained devices desirably have plugs, e.g., polyethylene plugs, inserted into their open ends to convert the hollow tube to substantially a rod like device.

EXAMPLE 1

A morantel tartrate containing device prepared according to Example 1 of U.S. Pat. No. 4,601,893 was constrained in a rolled-up configuration with a constraining means of this invention comprising a 8.9×7.6 cm wide laminate of 3M tape no. 900 and cellophane coated on both surfaces with nitrocellulose (product grade 345 PS-41). The ends of the tape when wrapped around the device overlapped 0.635 cm.

When placed in water at 40° C. as described above, the constraining means was removed in 40 minutes.

A similar device which had been stored at ambient temperature for 6 months required 57 minutes for removal of the constraining means when placed in 40° C. water.

EXAMPLE 2

The constraining means of a constrained device prepared according to Example 1, when administered to a fistulated ruminant, was observed to be removed within 40 minutes, resulting in unrolling of the device.

EXAMPLE 3

The experiment of Example 1 was repeated but using a tape in which 50 perforations, each 2 mm in diameter, were made in the overlapping ends.

The constraining means was removed in 15 minutes when the constrained device was placed in 40° C. water.

EXAMPLE 4

A device prepared according to Example 2 of U.S. Pat. No. 4,228,149 is constrained in a rolled configuration by a 8.9×7.6 cm wide laminate of 3M tape no. 405 and cellophane coated on both surfaces with nitrocellulose. The laminate was sufficiently long so that the ends overlapped 0.635 cm.

EXAMPLE 5

The procedure of Example 3 is repeated but using doubly coated repulpable tapes prepared using the adhesives of Example 29 of U.S. Pat. No. 4,569,960 and of Example 7 of U.S. Pat. No. 4,413,080.

EXAMPLE 6

Ten devices are prepared according to the procedure of Example 1 except that, prior to being constrained, the devices are annealed at 50° C. for 24 hours. The devices are then tested at varying time levels for their ability to unroll. All devices, even those stored at ambient temperature for 6 months, unrolled; i.e., the constraining means is removed, from their original 2.5 cm cross-section diameter to a cross-section diameter within one hour sufficient to prevent their regurgitation by a ruminant.

EXAMPLE 7

Devices prepared according to Example 1 were administered to 100 young ruminants (approximately 100 kg in weight). No difficulty was experienced in dosing the animals and no devices were regurgitated by any of the animals.

EXAMPLE 8

Twenty devices prepared substantially according to Example 1 were divided into two equal groups. Group A devices were placed in 40° C. water as described above and group B devices were administered to fistulated cattle, one device per animal. The times required for removal of the constraining means were recorded

| Group* | Average Removal Time | Range of Removal Time | Standard Deviation |
| --- | --- | --- | --- |
| A - in vitro | 31 minutes | 20-46 minutes | 8 minutes |
| B - in vivo | 51 minutes | 30-63 minutes | 9 minutes |

EXAMPLE 9

Nitrocellulose coated cellophane (BCL 345 PS 41) was coated with (Fitchburg Coated Products Inc., Scranton, PA 18501) WASH-AWAY ™ adhesive (a blend of polyvinyl methyl ether, maleic anhydride and a phosphate ester) to prepare a pressure sensitive constraining means with water soluble adhesive. A device from Example 1 of U.S. Pat. No. 4,601,893 was constrained by the above-mentioned constraining means. The constrained device when immersed in water at 40° C. underwent removal of the constraining means in 23 minutes.

We claim:
1. A laminate to act as a constraining device, comprising a water-permeable material having a low friction surface in the presence of water, said material being bonded by means of a water dispersible pressure sensitive adhesive to a first surface of a repulpable tape having first and second surfaces, said tape having a second layer of said water dispersible pressure sensitive adhesive on its second surface.

2. A laminate according to claim 1 wherein the low friction surface material is nitrocellulose.

3. The laminate according to claim 2 wherein the water-dispersible pressure sensitive adhesive comprises:
(I)
(a) a copolymer of monomers consisting essentially of
(1) about 90-20 parts by weight monomeric acrylic acid ester of non-tertiary alkyl alcohol the molecules of which have 1 to 4 carbon atoms; and
(2) about 10-80 parts by weight vinyl carboxylic acid monomer copolymerizable with said acrylic acid ester, at least a number of the carboxyl groups in said acid monomers sufficient to constitute about 3-22% the weight of said copolymer, having been neutralized by reaction with a secondary or tertiary alkanolamine containing at least 4 carbon atoms; and
(b) 0-400 parts by weight of at least one water-dispersible tack-promoting material selected from the group consisting of the oily plasticizing water-soluble polyoxyethylene compounds and the tackifying reaction products of acid rosins and alkanolamines; or
(II) the blended reaction product of
(a) 100 parts by weight of a copolymer of monomers consisting essentially of
(1) about 75-85 weight percent of at least one monomeric acrylic acid ester of nontertiary alkyl alcohol, and correspondingly,
(2) about 25-15 weight percent of vinyl carboxylic acid,
(b) about 35-100 parts by weight of acidic rosin or rosin derivative,
(c) sufficient potassium hydroxide to neutralize about 30-45% of the combined carboxyl groups of the copolymer and rosin or rosin derivative,
(d) sufficient sodium hydroxide, lithium hydroxide, or a combination of sodium and lithium hydroxide to neutralize about 20-45% of said carboxyl groups, and
(e) about 100-225 parts by weight of oily plasticizing water-soluble polyoxyethylene compound; or
(III) the blended reaction product of
(a) 100 parts by weight of a copolymer of monomers consisting essentially of
(1) about 60-85 weight percent of at least one monomeric acrylic acid ester of nontertiary alkyl alcohol having 4-14 carbon atoms, and correspondingly,
(2) about 40-15 weight percent of vinyl carboxylic acid,
(b) about 50 to 250 parts by weight of ethoxylated plasticizing components, sufficient to impart adhesion values such as to cause the adhesive to delaminate kraft paper, consisting essentially of at least one of the following:
(1) up to about 125 parts by weight, but not so much as to cause adhesive separation, of one or more OH-functional ethoxylated plasticizers and
(2) one or more electrolyte-tolerant complex and acidic esters of phosphoric acid and an ethoxylated nonionic surfactant, and
(c) alkaline hydroxide consisting essentially of (1) sodium hydroxide, lithium hydroxide, or both sodium hydroxide and lithium hydroxide, in an amount sufficient to enhance shear strength and minimize bleeding but insufficient to cause separation of any OH-functional ethoxylated plasticizer present, not exceeding about 0.07 hydroxyl equivalent if OH-functional ethoxylated plasticizer is the only plasticizing component present, and (2) potassium hydroxide in an amount sufficient to promote water solubility.

4. The laminate according to claim 3 wherein the pressure sensitive adhesive is that of claim 3, part I.

5. A laminate according to claim 4, said laminate having a flexible, water-permeable polymeric material bonded between the low friction surface material and the repulpable tape.

6. The laminate according to claim 5 wherein the low friction surface material is nitrocellulose and the flexible water-permeable polymeric material is a flexible cellophane.

* * * * *